US00PP10665P

United States Patent [19]

DeLeon

[11] Patent Number: Plant 10,665

[45] Date of Patent: Oct. 27, 1998

[54] AECHMEA PLANT NAMED 'GREY GHOST'

[75] Inventor: Nat DeLeon, Goulds, Fla.

[73] Assignee: Deleon's Bromeliads Inc., Goulds, Fla.

[21] Appl. No.: 797,513

[22] Filed: Feb. 7, 1997

[51] Int. Cl.[6] ..... A01H 5/00

[52] U.S. Cl. ..... Plt./88.8

[58] Field of Search ..... Plt./88.8

*Primary Examiner*—Elizabeth C. Kemmerer

*Attorney, Agent, or Firm*—Burns, Doane, Swecker & Mathis, L.L.P.

[57] ABSTRACT

A new and distinct variety of *Aechmea fasciata* is provided which forms a large abundantly branched pink-bracted inflorescence with contrasting blue flowers. The leaves are wide and spineless and prominently display silver-white coloration (as illustrated). The new variety can be readily distinguished from the 'DeLeon' variety (U.S. Plant Pat. No. 7,832) by the greater degree of branching of the inflorescence, a greater width of the leaves, and the presence of more silver-white coloration on the leaves.

3 Drawing Sheets

SUMMARY OF THE INVENTION

Aechmea plants are known to comprise a genus of over 168 species of evergreen perennials suitable for cultivation in the home or under glass. Aechmea may be terrestrial or epiphytic. For the most part the plants of the species vary in diameter from 12 to 18 inches to 3 or 4 feet and have rosettes of spiny edged leaves.

The flowers and bracts of Aechmea frequently have brilliant colors and may last up to several months. The range of colors for Aechmea is generally from yellow through orange but may also include pink, orange, red and red-purple. Tubular, three-petalled flowers may also appear but are usually short lived.

Aechmea may be advantageously grown as pot plants for greenhouse or home use. Typically the plants are shaded from direct sunlight and the central vase-like part of the leaf rosette is normally filled with water.

Aechmea is native to tropical America. Leaves of the Aechmea are usually formed as basal rosettes which are stiff and entire and in several vertical ranks. Aechmea have terminal spikes or panicles which are often bracted with the petals united in a tube that is longer than the calyx.

The new variety of *Aechmea fasciata* of the present invention was created during August 1990, at Miami, Fla. by artificial pollination wherein two parents were crossed which previously had been studied in the hope that they would contribute the desired characteristics.

The female parent (i.e., seed parent) was an unnamed *Aechmea fasciata* clone designated No. 79 (non-patented in the United States), and the male parent (i.e., pollen parent) was an unnamed *Aechmea fasciata* clone designated No. 87 (non-patented in the United States).

The seeds resulting from the above pollination were sown and small plants were obtained which were physically and biologically different from each other. Selective study during August 1992 resulted in the identification of a single plant of the new variety.

It was found that the new variety of the present invention possesses the following combination of characteristics:

(a) forms a large pink-bracted inflorescence that is abundantly branched, and (b) forms wide spineless leaves that heavily display a silver-white coloration.

The new variety of the present invention can be readily distinguished from the *Aechmea fasciata* 'DeLeon' variety (U.S. Plant Pat. No. 7,832). More specifically, the new variety forms an inflorescence that is more abundantly branched, and forms leaves that generally are wider and bear more silver-white coloration.

The new variety has been carefully evaluated and has been found to undergo asexual propagation at Goulds, Fla. beginning in October, 1992. More specifically, asexual propagation by the cutting of off-shoots growing from the base of the plant has shown that the characteristics of the new variety are stable and are strictly transmissible from one generation to another.

The new variety of the present invention has been named the 'Grey Ghost' variety.

The new 'Grey Ghost' variety has not been observed and tested under all possible environmental conditions to date. Accordingly, the phenotype may vary with variations in environmental conditions, such as temperature, light intensity, day length, humidity, etc., without any change in the genotype.

BRIEF DESCRIPTION OF THE PHOTOGRAPH

The accompanying photographs show as nearly true as it is reasonably possible to make the same in color illustrations of this character, a typical specimen of the plant and the foliage of the new variety. The plant was grown in a greenhouse at Goulds, Fla., while using growing conditions that are standard for the industry.

FIG. 1 illustrates the original plant of the new variety after 18 months of growth when finished in a 15 cm pot. The abundant branching propensity of the new variety is shown.

FIG. 2 illustrates a closer view of the inflorescence and leaves of the new variety. The attractive pink brachts are shown.

FIG. 3 illustrates for comparative purposes the upper leaf surface of the new variety on the right, and the upper leaf surface of the 'DeLeon' variety (U.S. Plant Pat. No. 7,832) on the left. It will be noted that the upper leaves of the new variety tend to be wider and to bear a more pronounced silver-white coloration that can be compared to the presence of more silver-white bands, or bars that extend across the leaves of the 'DeLeon' variety.

DETAILED DESCRIPTION

The chart used in the identification of colors is that of The Royal Horticultural Society (R.H.S.Colour Chart). The description is based upon the observation of the plant of FIG. 1 when grown at Goulds, Fla. under greenhouse conditions that are standard for the industry.

Classification: *Aechmea fasciata,* cv. 'Grey Ghost'.

Plant:

*Growth habit.*—Basal rosettes of strap-like leaves arranged around a central axis.

*Height.*—Approximately 50 cm. including inflorescence.

*Diameter.*—Approximately 70 to 90 cm.

Foliage:

*Leaf size.*—The basal leaves are approximately 35 to 45 cm. in length, and approximately 10 to 12 cm. in width.

*Leaf shape.*—The leaf blade is ligulate with a broadly rounded apiculate apex, slightly channeled, and the margins are entire and spineless.

*Leaf sheath.*—Broadly elliptic, approximately 8 to 12 cm. in length, and approximately 6 to 12 cm. in width.

*Leaf texture.*—The leaf blade is thick, coriaceous, and with very dense silver-white lepidote concentrated in bands and spots. Markings are particularly dense on the abaxial surface of the leaf where the white trichome covering obscures the leaf blade.

*Leaf color.*—The adaxial and abaxial surfaces are near Green Group 137B, but tend to be somewhat darker and greener.

*Number of leaves.*—The plant commonly produces approximately 16 leaves before producing an inflorescence.

*Roots.*—Wiry with fine laterals, and yellow-green changing to brown in coloration.

Bracts:

*Primary bracts.*—The primary bracts number approximately 20, are thin and papery, possess a surface that is densely appressed lepidote, possess a margin that is entire and spineless, and are located at the base of each branch spike. The length is approximately 6 to 12 cm. and the width is approximately 1.5 to 2 cm., and the shape is lanceolate or narrowly triangular with an acute tip. The adaxial and abaxial surfaces are near Red Group 55C in coloration.

*Floral bracts.*—The floral bracts underlying the flowers are coraceous, possess a surface that is pale appressed lepidote, possess a margin that is entire and spineless, commonly number approximately 176 and are approximately 2.5 to 3.5 cm. in length and approximately 1.2 to 1.5 cm. in width, and possess a triangular shape with an acute to attenuate tip. The adaxial and abaxial surfaces are near Red Group 54C in coloration.

*Scape bracts.*—The scape bracts are thin and papery, possess a surface that is densely appressed lepidote, possess a margin that is entire and spineless, encircle the scape, number approximately 7, are approximately 8 to 10 cm. in length and approximately 2 cm. in width, and possess a shape that is lanceolate with an acute to acuminate tip. The adaxial and abaxial surfaces are near Red Group 55D in coloration.

*Scape.*—The surface is densely covered with white floccose trichomes, the height is approximately 32 cm., the diameter is approximately 1.4 cm., and the color is near Red Group 53C.

*Branch spikes.*—The branches are sessile and are positioned at about 45° with respect to the main axis. The branches commonly extend up to approximately 5.5 cm. in length, and approximately 16 branch spikes commonly are present. Approximately 6 to 11 buds/flowers commonly are present on each branch spike.

*Shape of inflorescence.*—Densely digitate, pyramidal in configuration, commonly approximately 12 cm. in height, and commonly approximately 21 cm. in width.

Flowers:

*Calyx.*—Three sepals are present, approximately 10 to 12 mm. in length, and near Red Group 55D in coloration.

*Corolla.*—Tubular, three ligulate petals are present, approximately 26 to 28 mm. in length, and Blue Group 102D fading to Red-Purple Group 71D to black in coloration.

*Time of blooming.*—The flowering of mature plants commonly begins approximately 14 weeks after induction during the warm summer months, and approximately 16 to 17 weeks after induction during the cool winter months.

*Duration of inflorescence.*—The inflorescence commonly will hold its color approximately 3 to 4 months during the warm summer months, and approximately 4 to 6 months during the cool winter months.

Floral organs:

*Ovary.* —Inferior, possesses three locules, approximately 6 to 7 mm. in length, and white in coloration.

*Anthers.*—Approximately 5 mm. in length, and white in color.

Seed characteristics: Typical of the *Aechmea fasciata* species.

I Claim:

1. A new and distinct variety of *Aechmea fasciata* plant characterized by the following combination of characteristics:

(a) forms a large pink-bracted inflorescence that is abundantly branched, and (b) forms wide spineless leaves that heavily display a silver-white coloration;

substantially as herein illustrated and described.

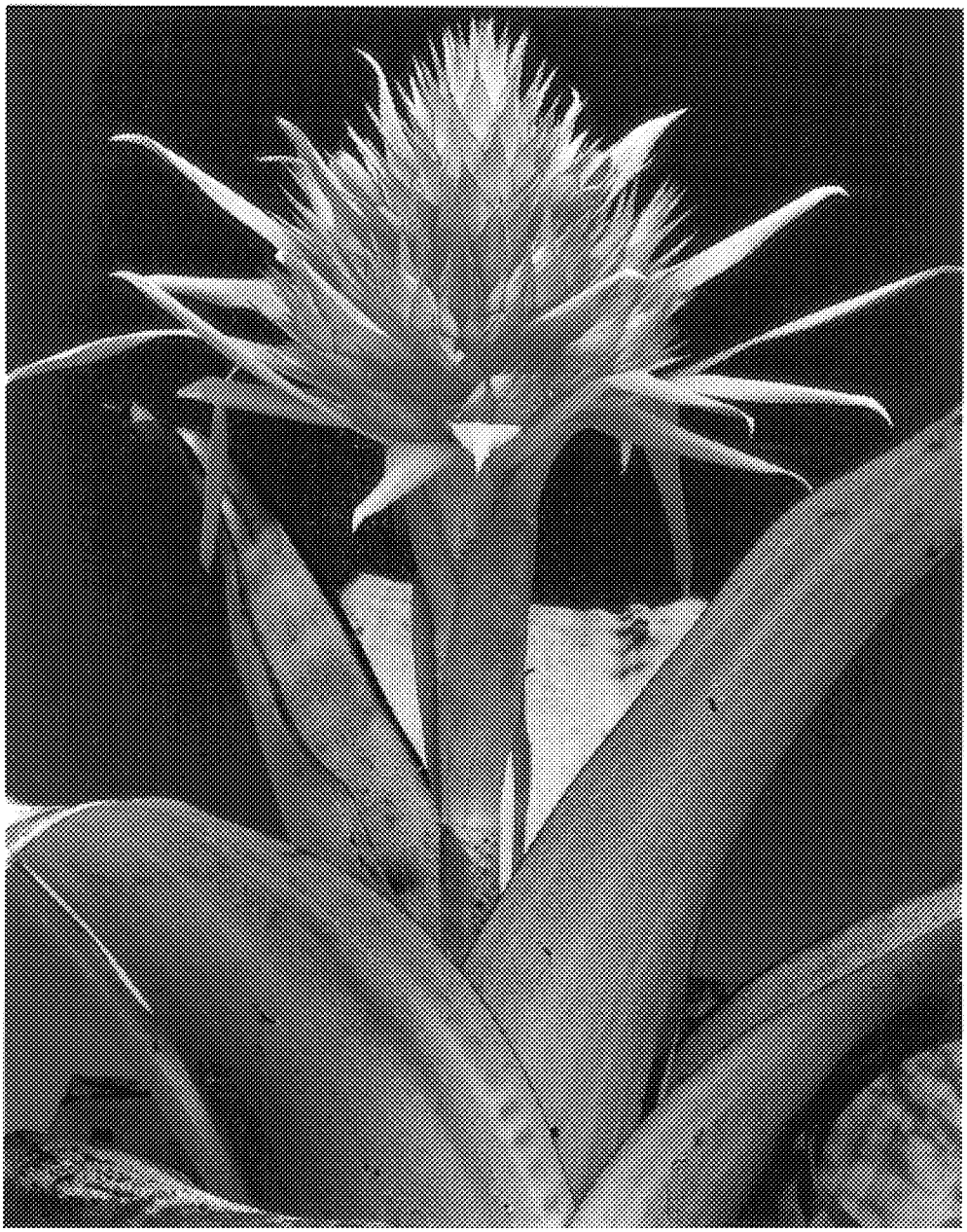

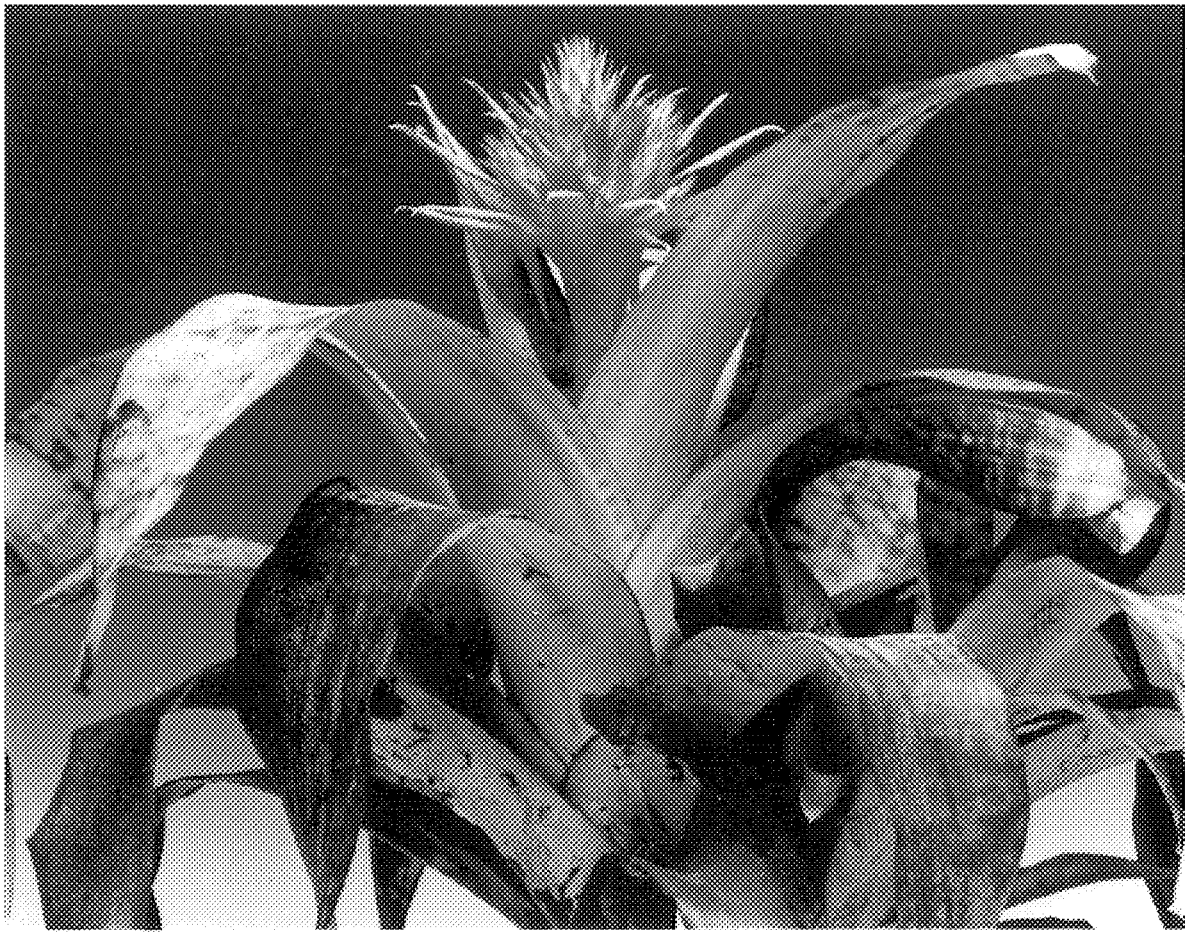

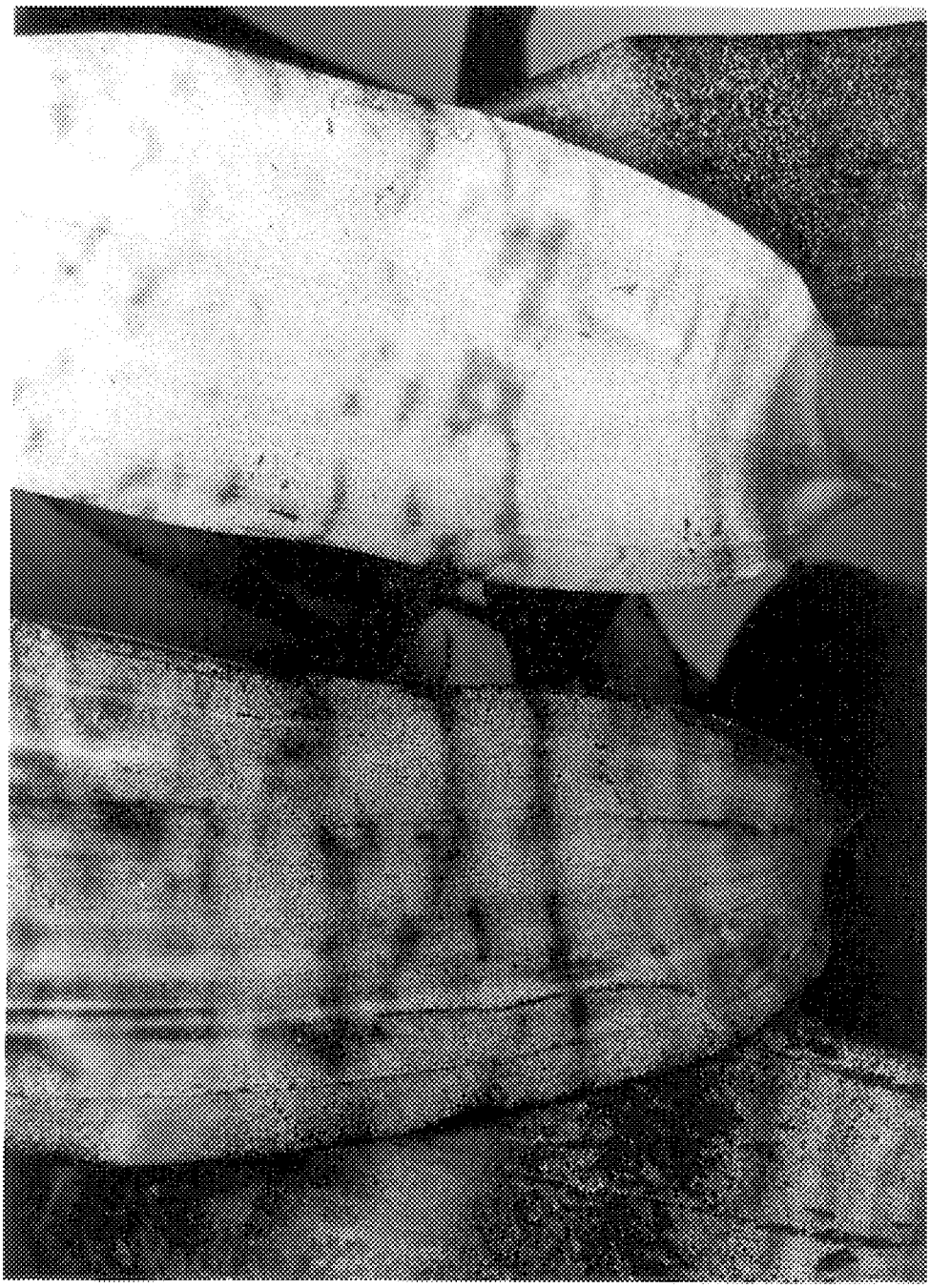

* * * * *